(12) United States Patent
Jarva et al.

(10) Patent No.: US 11,096,637 B2
(45) Date of Patent: Aug. 24, 2021

(54) X-RAY IMAGING APPARATUS AND PATIENT SUPPORT SAFETY MECHANISM

(71) Applicant: PLANMECA OY, Helsinki (FI)

(72) Inventors: Mikko Jarva, Helsinki (FI); Kari Malmen, Helsinki (FI); Lauri Seppala, Helsinki (FI); Tero Pihlajamaki, Helsinki (FI); Pentti Hyvarinen, Helsinki (FI); Timo Muller, Helsinki (FI)

(73) Assignee: PLANMECA OY, Helsinki (FI)

(*) Notice: Subject to any disclaimer, the term of this patent is extended or adjusted under 35 U.S.C. 154(b) by 157 days.

(21) Appl. No.: 16/494,470

(22) PCT Filed: Mar. 19, 2018

(86) PCT No.: PCT/FI2018/050199
§ 371 (c)(1),
(2) Date: Sep. 16, 2019

(87) PCT Pub. No.: WO2018/167376
PCT Pub. Date: Sep. 20, 2018

(65) Prior Publication Data
US 2021/0121141 A1    Apr. 29, 2021

(30) Foreign Application Priority Data
Mar. 17, 2017 (FI) .................. 20175242

(51) Int. Cl.
*A61B 6/00* (2006.01)
*A61B 6/14* (2006.01)
(Continued)

(52) U.S. Cl.
CPC .............. *A61B 6/14* (2013.01); *A61B 6/0407* (2013.01); *A61B 6/102* (2013.01); *A61B 6/501* (2013.01); *A61B 6/547* (2013.01)

(58) Field of Classification Search
CPC ......... A61B 6/14; A61B 6/0407; A61B 6/102; A61B 6/501; A61B 6/547
See application file for complete search history.

(56) References Cited

U.S. PATENT DOCUMENTS

2002/0032453 A1* 3/2002 Cosman ............... A61B 6/0421
606/130

FOREIGN PATENT DOCUMENTS

| JP | H05110 U | 1/1993 |
| JP | 2008092990 A | 4/2008 |
| KR | 2016072902 A | 6/2016 |

OTHER PUBLICATIONS

International Search Report for PCT Application No. PCT/FI2018/050199, dated Jul. 4, 2018, 3 pages.

* cited by examiner

*Primary Examiner* — Dani Fox
(74) *Attorney, Agent, or Firm* — Fay Sharpe LLP

(57) ABSTRACT

The invention concerns an X-ray imaging apparatus for imaging a skull or a partial area of the skull, which apparatus comprises between the X-ray source and detector a patient support means (17). The patient support means (17) comprise a rear rest structure (170) containing a support part (171) arranged to get positioned at occipital area and a safety mechanism (173) in an area between its mounting point to the X-ray imaging apparatus (10) and said support pan (171). The safety mechanism (173) is arranged to go off when a force greater titan predetermined is acting on said support pan (171) and to release said support part (171) from its patient support position.

19 Claims, 3 Drawing Sheets

(51) Int. Cl.
*A61B 6/10* (2006.01)
*A61B 6/04* (2006.01)

X-RAY IMAGING APPARATUS AND PATIENT SUPPORT SAFETY MECHANISM

FIELD OF INVENTION

The invention relates to a patient support for an odontological X-ray apparatus according to the preamble of claim 1.

BACKGROUND OF INVENTION

The history of medical X-ray imaging originates approximately to the time of inventing X-ray radiation. For more advanced ways of imaging e.g. in the dental field, the developing of panoramic X-ray imaging begun for over a half century ago. The advancement of digital imaging especially in the 1990s brought digital X-ray imaging apparatuses also to dental practices. The latest development in the dental field has been generalization of the cone-beam computed tomography apparatuses designed for three-dimensional imaging of teeth and other bones of the cranial area. Among other things, computed tomography enables imaging both the cranial bones and teeth as well as soft tissues. Along with many other reasons, the generalization of odontological computed tomography imaging has been contributed, among other things, by being able to get soft tissues of the cranial area better visible in computed tomography images than e.g. in conventional radiographs of the cranial area.

In connection with the X-ray imaging of persons, one must try to provide for not to expose the patient to radiation more than necessary for making a diagnosis. The amount of the radiation dose can be affected, among other things, by choosing the best applicable imaging technology for each situation and by developing the actual imaging techniques. A typical problem causing extra radiation stress is, however, a failure in imaging, whereby the patient has to be re-imaged. As the imaging may last even about twenty seconds, a typical reason for the failure in imaging is that the patient moves or stirs during the imaging.

The field of odontology commonly employs X-ray apparatuses where the patient sits or stands positioned at a patient support means during the imaging. Commonly found structures in such support means are e.g. a chin support, a bite support, support rails which position on the patient's temples and mostly provide sideways pointed support, and a forehead support. Known are also structures which are arranged to support the occiput.

In odontological panoramic and cone-beam computed tomography imagings, for instance, where the imaging means rotate around the patient's head and the imaging event typically lasts of the order of 10-20 seconds, the large-size C-anti rotating around the head in front of the patient's face can easily frighten the patient. Also otherwise due to the duration of the imaging event, the patient might try to move his/her head out of its place or turn it during an exposure.

In many patient support arrangements according to prior art, the primary purpose is to position the anatomy being imaged to a desired point while the structure has not necessarily been designed especially for assisting keeping the head in its place but for the most in some specific direction or directions. The support structure can also be such that it is challenging to use it as a support for patients of different sizes and/or a patient it may find it uncomfortable. It is also possible that a structure designed for a particular support function can impede the operations of the person assisting the imaging e.g. when the purpose is to use in the imaging also some other support structure for additional support, or when the use of the support structure requires repetitive moving to the other side of the patient. The support structures are also associated with patient safety aspects which have not necessarily been fully considered in all solutions.

BRIEF DESCRIPTION OF INVENTION

The object of the invention is to provide a novel kind patient support arrangement including a safety mechanism for an odontological X-ray apparatus.

A patient support arrangement according to the invention has been designed to take into account safety risks presented by a certain kind of imaging situation. As an example of advantages provided by the invention one can refer to wheelchair users the positioning of whom for imaging can be challenging in arrangements according to prior art. On the other hand the invention with its preferable embodiments presents a support arrangement by which imaging of a wheelchair user can be easily implemented with a similar support as when imaging of e.g. a patient standing independently on his/her own two feet and which, considering an X-ray imaging apparatus which is also arranged with means to image the patient optically, offers a possibility to arrange free space to image both the facial area and the area of temples and ears without at the same time imaging also the patient support means.

The principal characteristics of the invention are described in the accompanying patent claims.

Next, the invention and its preferable embodiments will be described in more detail and with reference to the attached figures.

DETAILED DESCRIPTION OF INVENTION

Figure 1:
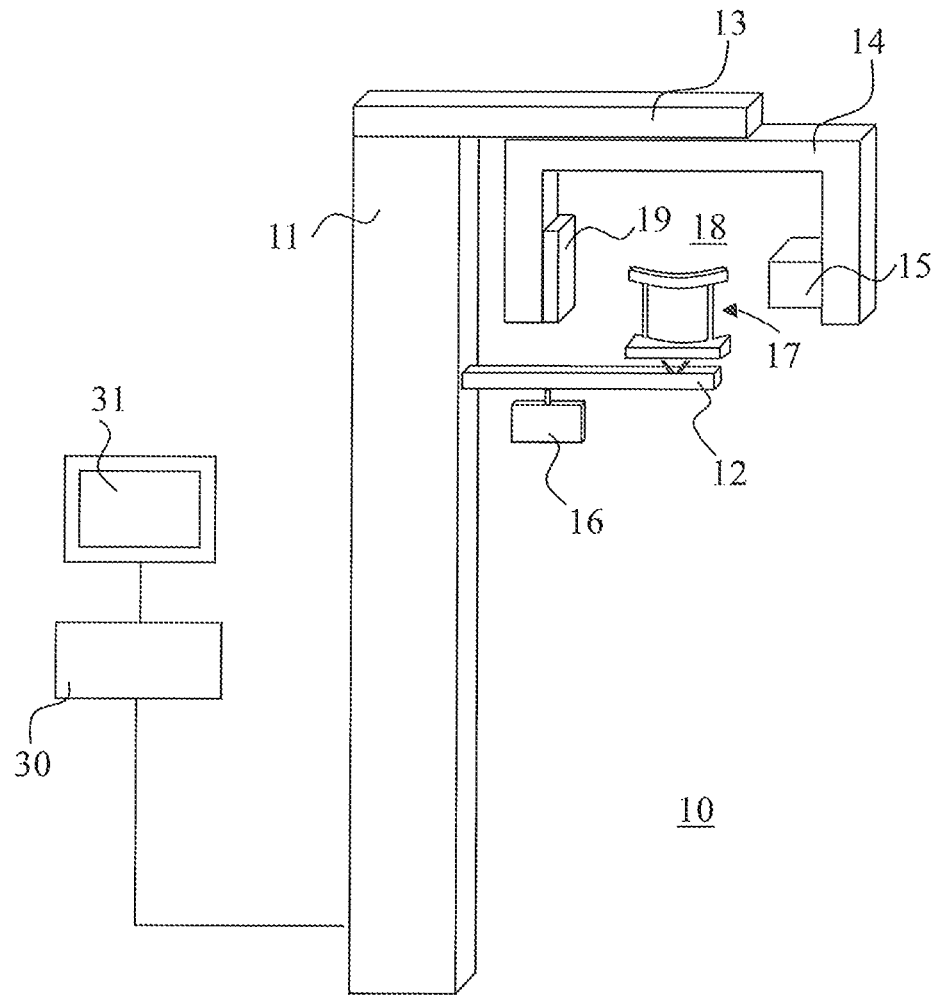
FIG. 1 shows a typical odontological X-ray imaging apparatus according to prior art, its basic structure including a support structure, an arm part supporting imaging means and a patient support station.

FIG. 1 shows an X-ray imaging apparatus 10 including a vertical support structure 11 from which horizontally extend a structure 12 supporting patient support means 17 and an arm part 13 which supports a structure supporting imaging means, an arm part 14. To the arm part 14 supporting the imaging means are arranged at a distance from each other the X-ray imaging means of the apparatus, i.e. an X-ray radiation source 15 and a receiver of X-ray image information 19, which have been positioned to the apparatus with respect to the patient support means 17 such that to the apparatus is formed an imaging station 18, which takes its position between the X-ray radiation source 15 and the receiver of X-ray image information 19 such that a beam produced by the X-ray radiation source 15 may be directed to pass via the imaging station 18 towards the receiver of X-ray imaging information 19. The akin part 14 supporting these imaging means is arranged rotatable and also its position with respect to the structure supporting it 13 and/or the patient support station 18 may be arranged changeable. The apparatus includes control means, of which, FIG. 1 shows a control panel 16 positioned in connection with the arm supporting the patient support means 12. The apparatus 10 can be arranged via a cable into connection with a computer 30 which can be arranged with a means for processing image information produced by the apparatus and a display 31 which can display images.

Figure 2:
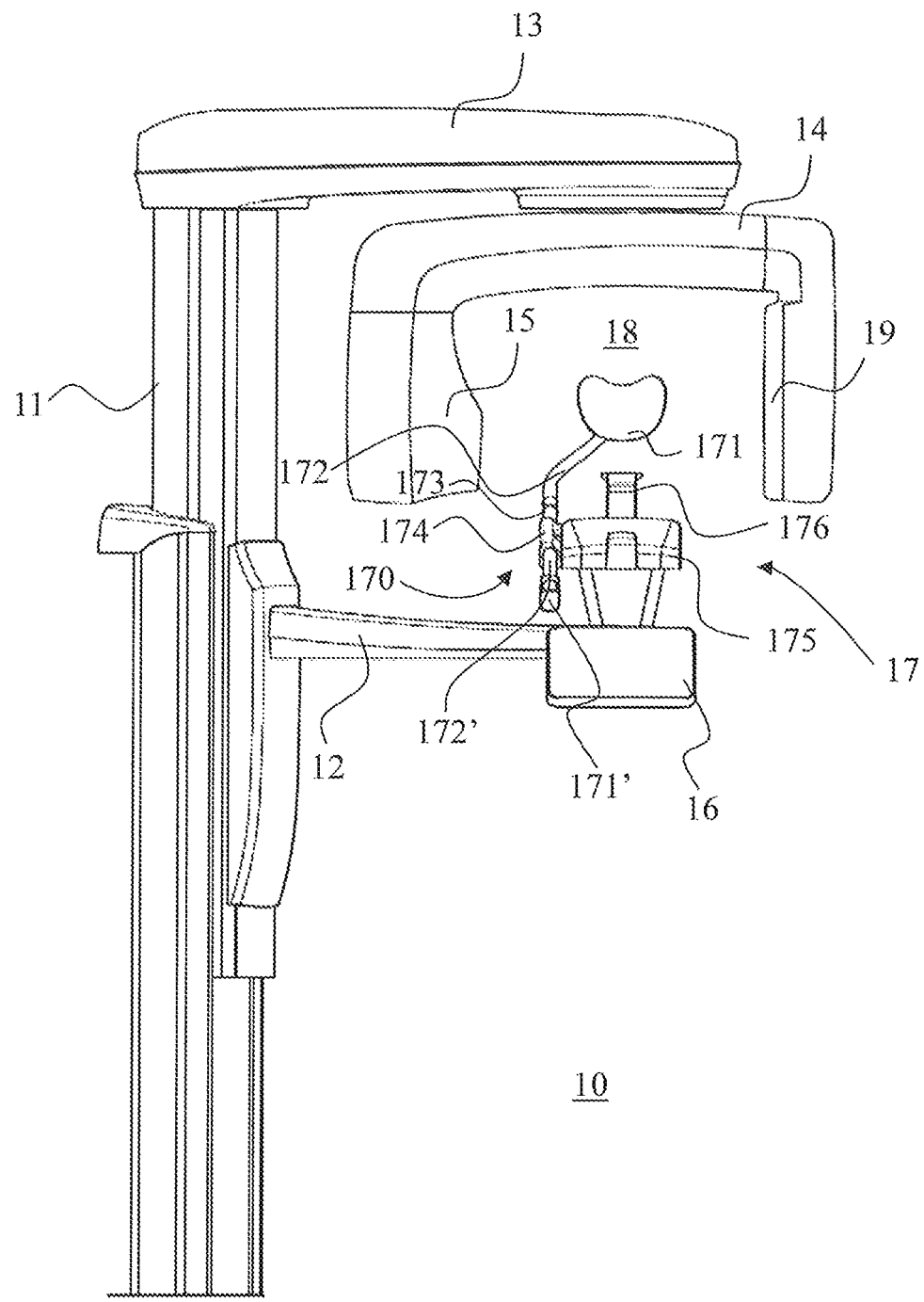
FIG. 2 shows an arrangement according to the invention where a patient support structure comprising an occipital support is mounted to an odontological X-ray imaging apparatus.
Figure 3:
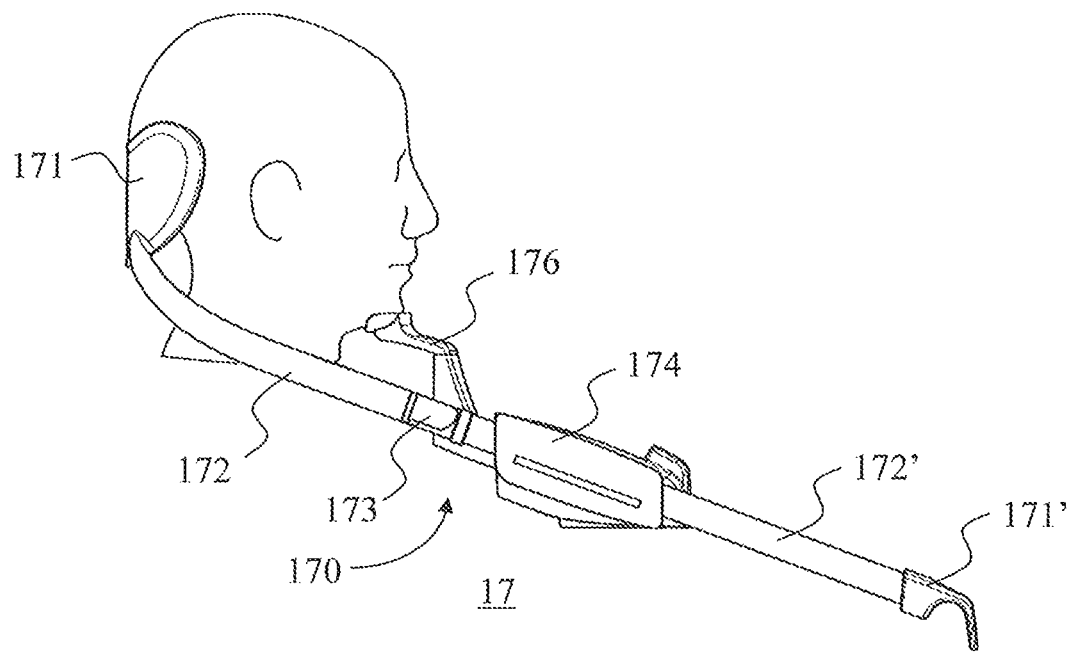
FIG. 3 shows a side view of a patient support structure applicable for use in the invention.

The basic structure of the X-ray imaging apparatus shown in FIG. 2 corresponds to the basic structure of the apparatus shown in FIG. 1. As an essential difference in view of the patient support structure comprising a forehead support shown in FIG. 1, FIG. 2 shows a rest structure setting on the occiput. FIG. 3 shows a side view of such patient support structure setting on the occiput.

A rear rest structure 170 shown in FIGS. 2 and 3 comprises an actual support part 171 setting against the skull and a supporting structure 172 diverging from it.

In the embodiment according to FIGS. 2 and 3, the supporting structure 172 consists of an elongated structure, a first end of which containing the above-mentioned support part 171 and which extends on a different side of the imaging station 18 as where the support part 171 is located. A second end 171' of the supporting structure 172 of the rear rest structure extends for a distance past its mounting point to the X-ray imaging apparatus 10. The shape of the supporting structure 172 can be some other than the one shown in FIGS. 2 and 3 and can e.g. only comprise an elongated, possibly arm-like structure.

In the embodiment according to FIGS. 2 and 3, a surface of the support part 171 of the rear rest structure pointing towards the imaging station 18 is arranged curved in the direction of the imaging station 18, substantially to correspond a curvature of a skull. The radius of curvature of that surface curving towards the imaging station 18 can be implemented such that it is not constant but the surface comprises an area in the middle part of the curve where the radius of curvature is smaller than the one in the edge area of the curve. Implemented as such, the support part 171 adapts better than an evenly curved surface to support skulls of different sizes and also gives support to prevent the head from turning.

In FIG. 2, the rear rest structure 170, in more detail the supporting structure 172 contained by it, is mounted to the X-ray imaging apparatus by a mounting structure 174 which can be arranged to enable adjustment of the mounting point of the rear rest structure 170 to the X-ray imaging apparatus. This way, a section 172' of the rear rest structure 170 extending past its mounting point to the X-ray imaging apparatus 10 functions as a practical grabbing means when the mounting structure 174 of the rear rest structure has been arranged to enable a detachable mounting of the rear rest support 170 and when wanting to adjust the position of the support structure 171.

FIGS. 2 and 3 illustrate the implementation of the rear rest structure 170 such that the support part 171 of the rear rest structure 170 sets on a higher horizontal plane than its mounting point to the X-ray imaging apparatus 10.

In one preferred embodiment of the invention, the supporting structure 172 of the rear rest structure 170 comprises an elongated arm-like structure which sets at its mounting point to the X-ray imaging apparatus 10 such that the supporting structure 172 extends towards the support part 171 at an angle of 15-25 degrees with respect to the horizontal plane. Preferably, this angle is about 20 degrees which approximately equals the angle of a line connecting the anatomies 'tip of chin' and 'middle of occiput' with respect to the horizontal plane, when the head is in an upright position and the gaze towards the horizon. The measure from the 'tip of chin' to the 'middle of occiput' can be utilized when adjusting imaging parameter values used in X-ray imaging to correspond characteristics of the anatomy being imaged at a time.

When the rear rest structure 170 and its mounting to the X-ray apparatus is implemented such that the support part 171 of the rear rest structure moves when adjusting its position on a line or on a plane having the angle with respect to the horizontal plane of approximately said about 20 degrees, such as between 15-25 degrees, an arrangement is provided by means of which it is possible to obtain with simple operations particularly the measure from the 'tip of chin' to the 'middle of occiput' of an anatomy being imaged at a given time, which measure illustrates the size differences between skulls better than e.g. the differences in skulls' horizontal dimension. One way to implement this kind of an arrangement is to arrange the supporting structure 172 of the rear rest structure comprising a substantially linear part which is arranged movable but also mountable to a groove or a sleeve of substantially equal size, which then operates as the mounting structure 174 of the rear rest structure and which is arranged to the X-ray apparatus such that said substantially linear part of the supporting structure 172 of the rear rest structure is positioned at the above-mentioned angle with respect to the horizontal plane.

In one embodiment of the invention, the patient support means 17 of the X-ray imaging apparatus comprises a chin support structure or a bite support structure 176 and the line or the plane mentioned in the previous chapter is arranged to pass substantially via the point to which the patient's anatomy is designed to be positioned to said chin or bite support structure 176.

To the X-ray imaging apparatus, it is possible to arrange identification means to indicate or identify the above-discussed measure—or some other known distance the correlation of which to said distance is known. Thus, when the distance of the support part 171 of the rear rest structure from the mounting point of the rear rest structure 170 to the X-ray apparatus is arranged adjustable, it is possible to arrange to the X-ray imaging apparatus identification means to indicate or identify this distance, or the distance of the support part 171 from some other reference structure of the X-ray apparatus. In connection with the mounting point of the rear rest structure 170 to the X-ray apparatus, foe example, there may be means to measure or observe the distance of some identifiable point in the rear rest structure 170 from a known reference point, or the rear rest structure 170 may be arranged with a scale arranged to always be measured from the same point of the X-ray apparatus which then directly gives the position of the rear rest structure 170 within its operation area and, thus, e.g. the distance from the support part 170 of the rear rest structure to the chin or bite support of the X-ray apparatus.

That measure may also be basis for e.g. a warning signal on that a motion path of the imaging means 15, 19 intended for use in X-ray imaging is getting so close to the patient that it is best to consider adjusting the path of movement to be different, before starting the imaging. That measure may thus indicate that the rear rest structure 170 is positioned at a place which is in the area of the part of movement of the imaging means 15, 19 during imaging, or at a distance closer than predetermined to such an area.

FIG. 3 shows a jointed structure 173 arranged in the area between the mounting point of the rear rest structure 170 to the X-ray imaging apparatus 10 and the support part 171 of the rear rest structure which is arranged to operate as a safety mechanism 173 in the case of the patient passing out or having a panic attack during the imaging. If the patient has been positioned e.g. both in the chin and rear rest support, there is a theoretical risk of injury if neither of the supports give way when the patient is wedged between those support structures. Hence, such a safety mechanism can be arranged to go off e.g. when force greater than predetermined is acting on the support part 171 of the rear rest structure, the identification of which situation may then release the support part 171 from its patient support position. E.g. the above-mentioned jointed structure 173 arranged in the supporting structure 172 of the support part 171 of the rear rest structure 170 can be arranged to turn when a moment acting on it exceeds a specified limit value.

In the embodiment according to FIG. 2, the supporting structure 12 of the patient support means 17 is arranged with a second mounting structure 175 to which a chin support or a bite support 176 can be mounted.

In the embodiment of FIG. 2, the supporting structure 172 of the support part 171 of the rear rest structure 170 is also mounted to a mounting structure 174 arranged in connection with the patient support means 17, namely in connection with a mounting structure 175 of the bite or chin support 176, but the mounting structure 174 of the rear rest structure can also be arranged elsewhere, e.g. to the supporting structure 12 of the patient support means 17 extending straight from the substantially vertical frame part 11 of the X-ray apparatus.

The invention claimed is:

1. An X-ray imaging apparatus for imaging a skull or a partial area of the skull, which apparatus comprises:
   a substantially vertical frame part;
   an X-ray radiation source and a receiver of X-ray radiation which together form X-ray imaging means;
   a control system of the X-ray imaging means;
   an imaging station positioned in an area between the X-ray radiation source and the receiver of X-ray radiation;
   a patient support means arranged ire connection with the imaging station for supporting an anatomy being imaged;
   which patient support means for supporting the anatomy being imaged, comprise a rear rest structure containing a support part, which support part is arranged to get positioned at occipital area, characterized in that said rear rest structure comprises a safety mechanism in the an area between its mounting point to the X-ray imaging apparatus and said support part which safety mechanism is arranged to go off when a force greater than predetermined is acting on said support part and then to release said support part from its patient support position.

2. An X-ray imaging apparatus according to claim 1, characterized in that said safety mechanism comprises a jointed structure that has been arranged to turn when a moment acting on it exceeds a specified limit value.

3. An X-ray imaging apparatus according to claim 1, characterized in that said rear rest structure comprises a first supporting structure, which extends to different side of the imaging station than where said support part is located.

4. An X-ray imaging apparatus according to claim 1, characterized in that said first supporting structure is implemented such that said support part positions on a horizontal plane higher than the mounting point of the first supporting structure to the X-ray imaging apparatus.

5. An X-ray imaging apparatus according to claim 1, characterized in that said first supporting structure comprises an elongated structure, a first end of which contains said support part and a second end which extends a distance past its mounting point to the X-ray imaging apparatus.

6. An X-ray imaging apparatus according to claim 1, characterized in that said first supporting structure comprises an elongated structure or is formed of an elongated structure which is positioned to its mounting point to the X-ray imaging apparatus such that the supporting structure extends towards said support part at an angle of 15-25 degrees with respect to the horizontal plane.

7. An X-ray imaging apparatus according to claim 6, characterized in that said angle is about 20 degrees.

8. An X-ray imaging apparatus according to claim 1, characterized in that the rear rest structure and its mounting to the X-ray apparatus is implemented such that the support part of the rear rest structure moves when adjusting its position on a line or on a plane the angle of which with respect to the horizontal plane is between 15-25 degrees.

9. An X-ray imaging apparatus according to claim 8, characterized in that said angle is about 20 degrees.

10. An X-ray imaging apparatus according to claim 8, characterized in that said patient support means comprise a chin support structure or a bite support structure and said straight line or plane is arranged to pass via substantially that point in which the patient's anatomy is designed to be positioned in said support structure.

11. An X-ray imaging apparatus according to claim 1, characterized in that said supporting structure of the rear rest structure is arranged to comprise a movably arranged substantially linear part, on the other hand, mountable to a groove or, a sleeve substantially of equal size arranged in the X-ray apparatus such that said substantially linear part of the supporting structure of the rear rest structure gets positioned at an angle of 15-25 degrees.

12. An X-ray imaging apparatus according to claim 11, characterized in that said angle is about 20 degrees.

13. An X-ray imaging apparatus according to claim 1, characterized in that a surface of said support part pointing towards the imaging station is arranged curved in the direction of the imaging station.

14. An X-ray imaging apparatus according to claim 13, characterized in that the radius of curvature of the surface of said support part curving towards the imaging station comprises an area in the middle part of the curve where the radius of curvature is smaller than in the edge area of the curve.

15. An X-ray imaging apparatus according, to claim 1, characterized in that the distance of said support part from the mounting point of the rear rest structure to the X-ray apparatus is arranged adjustable, and to the X-ray imaging apparatus is arranged an identification means to indicate or identify this distance or the distance of the support part from some other reference structure of the X-ray apparatus.

16. An X-ray imaging apparatus according to claim 15, characterized in that to the control system of the X-ray imaging apparatus is arranged a means for receiving information on said distance from said identification means and, based on this information, to perform at least one of the following:
   adjusting imaging parameter values intended for use in X-ray imaging,
   adjusting a motion path of the imaging means which is intended to be used in X-ray imaging,
   indicating that said rear rest structure is positioned at a place which is in the area of the motion path of the imaging means during imaging or at a predetermined distance closer to such an area.

17. An X-ray imaging apparatus according to claim 1, characterized in that from said substantially vertical frame part extends a supporting structure of the patient support means, to which or to in connection with which arranged first mounting structure said first supporting structure is arranged to be mountable.

18. An X-ray imaging apparatus according to claim 17, characterized in that into connection with said supporting structure of the patient support means is arranged a second mounting structure to which a bite support or a chin support is arranged to be mounted.

19. An X-ray imaging apparatus according to claim 18, characterized in that said first mounting structure is arranged into connection with said second mounting structure.

* * * * *